United States Patent [19]
Matsuura et al.

[11] Patent Number: 6,042,851
[45] Date of Patent: Mar. 28, 2000

[54] PROCESS FOR PRODUCING PACKED TOFU

[75] Inventors: Masaru Matsuura; Masaoki Sasaki; Jun Sasaki; Tomoko Takeuchi, all of Chiba Pref., Japan

[73] Assignee: Kikkoman Corporation, Chiba Pref., Japan

[21] Appl. No.: 09/201,840

[22] Filed: Dec. 1, 1998

[30] Foreign Application Priority Data

Dec. 3, 1997 [JP] Japan .................................. 9-347335

[51] Int. Cl.⁷ .......................... A23C 3/023; A23C 9/137; A23B 9/28; A23L 1/20
[52] U.S. Cl. ................. 426/8; 426/34; 426/42; 426/46; 426/407; 426/634
[58] Field of Search ..................... 426/418, 392, 426/407, 520, 34, 42, 44, 46, 8, 629, 634

[56] References Cited

U.S. PATENT DOCUMENTS 4,917,904  4/1990  Wakameda et al. ...................... 426/7
5,055,310  10/1991  Nonaka et al. .......................... 426/46

FOREIGN PATENT DOCUMENTS 7-241168  9/1995  Japan .

*Primary Examiner*—Keith D. Hendricks
*Attorney, Agent, or Firm*—Young & Thompson

[57] ABSTRACT

A process for producing packed tofu includes the steps of mixing soybean milk that has been heat-sterilized and cooled with (A) 0.01 to 0.3% by weight by volume of at least one coagulant selected from the group consisting of natural bittern, magnesium chloride, magnesium sulfate, calcium chloride, calcium primary phosphate, calcium sulfate, and calcium lactate and (B) 0.1 to 5 units, per gram of soybean milk protein, of transglutaminase either simultaneously or in the order (A) then (B), then packing and sealing the mixture in a container, then coagulating the mixture in the sealed container at a temperature of 70° C. or lower by the action of the coagulant and transglutaminase, and thereafter heating the coagulated mixture to 75° C. or higher in the sealed container to deactivate the transglutaminase and to complete the coagulation by the coagulant.

4 Claims, 7 Drawing Sheets

PROCESS FOR PRODUCING PACKED TOFU

BACKGROUND OF THE INVENTION

1. Field of the Invention

The present invention relates to a novel process for producing packed tofu, particularly a process for producing long-life packed tofu from sterilized soybean milk.

2. Description of Related Art

Tofu (bean curd) is largely divided into two types: momen (pressed) tofu and silken tofu. Tofu is also divided according to the process of preparation into (1) cut tofu which is obtained by coagulating soybean milk in a mold and, after immersing in water, cutting to size and (2) packed tofu which is obtained by filling a small container of given size with soybean milk containing a coagulant, sealing the container, and allowing the soybean milk to coagulate in the container.

Conventional tofu generally keeps only 2 to 3 days at most even if kept at a temperature of 10° C. or lower. In order to prolong the storage life of tofu, processes for producing sterile packed tofu from soybean milk having been sterilized at high temperature or retort tofu from non-sterilized soybean milk have been proposed.

The flavor of tofu is influenced by not only the quality of raw soybeans and water but also by the kind of the coagulants. In general, tofu prepared by using, as a coagulant, natural bittern, magnesium chloride, magnesium sulfate, calcium chloride, calcium primary phosphate, calcium sulfate, and calcium lactate, is more flavorful than that prepared by using glucono-δ-lactone. The natural bittern, magnesium chloride, magnesium sulfate, calcium chloride, calcium primary phosphate, calcium sulfate, and calcium lactate are generalized and referred to as "bittern" hereinafter. However, since bittern is generally quick to work, it causes partial coagulation on addition, and therefore it is difficult to use bittern in the production of packed tofu.

In the production of packed tofu, soybean milk to which the coagulant has been added is packed into a container and coagulated by heat. Uneven coagulation will occur unless the soybean milk containing the coagulant is rapidly packed into the container and heat-coagulated. Therefore, various manipulations would be required to avoid such uneven coagulation. Besides, the above-described bittern tastes bitter or astringent if added in a large amount, and tends to impair the taste of packed tofu, which is prepared by coagulating soybean milk in a container.

Where, in particular, long-life tofu is produced from soybean milk having been sterilized in high temperature, a larger amount of bittern is required for coagulation than used for general soybean milk because the gel-formation ability of soybean milk is reduced to ⅓ to ⅕ by the sterilization. In this case, the above-mentioned disadvantage of using bittern in packed tofu would be exaggerated.

Thus, it has been practically impossible to produce packed tofu with satisfactory palatability and texture by using sterilized soybean milk containing bittern as the main coagulant. At present, slow-acting glucono-δ-lactone has been used as a main coagulant in the production of long-life packed tofu.

Japanese Patent Laid-Open No. 241168/95 discloses a process for producing tofu aiming at energy saving, in which transglutaminase is added to sterilized soybean milk in as large an amount as 10 to 40 units per gram of protein so that the sterilized soybean milk can be coagulated at room temperature. However, the tofu obtained by this process is seriously different in texture from one prepared by using bittern as the main coagulant, as will be demonstrated in Test Examples hereinafter given. The difference in texture is attributed to the decided difference of transglutaminase from bittern in mode of binding reaction among protein molecules induced thereby.

SUMMARY OF THE INVENTION

An object of the present invention is to provide a process for producing packed tofu from sterilized soybean milk and bittern, which has a long storage life and yet retains satisfactory flavor and texture.

As a result of extensive investigation, the inventors of the present invention have found that the objective tofu is accomplished by adding to sterilized soybean milk a specific amount of bittern and a specific amount of transglutaminase (hereinafter abbreviated as TG). The present invention has been completed based on this finding.

The present invention provides a process for producing packed tofu which comprises mixing heat-sterilized and cooled soybean milk with (A) 0.01 to 0.3% by weight by volume (w/v %) of at least one coagulant selected from the group consisting of natural bittern, magnesium chloride, magnesium sulfate, calcium chloride, calcium primary phosphate, calcium sulfate, and calcium lactate and (B) 0.1 to 5 units, per gram of soybean milk protein, of TG either simultaneously or in the order (A) then (B), packing the mixture into a container, coagulating the packed mixture at a temperature of 70° C. or lower by the action of the coagulant and TG, heating the coagulated mixture to 75° C. or higher to deactivate the TG and to complete the coagulation by the coagulant.

The present invention also provides a process for producing sterile packed tofu which comprises mixing heat-sterilized and cooled soybean milk with (A') 0.01 to 0.3 w/v % of at least one sterilized coagulant selected from the group consisting of natural bittern, magnesium chloride, magnesium sulfate, calcium chloride, and calcium primary phosphate and (B) 0.1 to 5 units, per gram of soybean milk protein, of TG either simultaneously or in the order (A) then (B), in a sterile atmosphere, packing the mixture into a container in a sterile atmosphere, sealing, maintaining the packed mixture at 35 to 70° C. for 5 to 120 minutes to allow the mixture to coagulate by the action of the coagulant and TG, heating the coagulated mixture at 75 to 110° C. for 5 to 120 minutes to deactivate the TG and to complete the coagulation by the coagulant.

The present invention provides packed tofu which has the flavor and texture essential to traditional bittern-added tofu and yet can keep long.

DETAILED DESCRIPTION OF THE INVENTION

Now the present invention will be described in detail according to the process of the preparation.

[Preparation of Sterile Soybean Milk]

Soybean milk used as a starting material is prepared in a conventional manner. That is, soaked soybeans, skinned soybeans or unsoaked soybeans are ground in a grinder together with water, and the resulting slurry is heated at 90 to 120° C. for about 0.1 to 10 minutes, followed by filtration to obtain soybean milk.

Although most of the microorganisms attached to soybeans are killed by the heat treatment, presence of heat-resistant soil bacteria or heat-resistant soil endospores is expected. Therefore, the soybean milk is subjected to ultra high temperature (UHT) treatment at 130 to 160° C. for 1 to 10 seconds to prepare sterile soybean milk.

The protein concentration of soybean milk is 5 to 10% by weight, preferably 6 to 8% by weight.

[Preparation of Bittern]

At least one coagulant selected from the group consisting of natural bittern, magnesium chloride, magnesium sulfate, calcium chloride, calcium primary phosphate, calcium sulfate, and calcium lactate is used in the form of an aqueous solution having a concentration of 5 to 70% by weight.

The storage properties of packed tofu will be further improved by using natural bittern, magnesium chloride, magnesium sulfate, calcium chloride or calcium primary phosphate after sterile filtration with a germ-free filter (e.g., Membrane Filter produced by Nippon Millipore K.K.).

Natural bittern is preferably subjected to sterile filtration after it is preliminarily filtered to remove insoluble matter.

[Preparation of TG]

A commercially available TG species is used in the form of an aqueous solution having a concentration of 1 to 50% by weight. The storage properties of the packed tofu will be further improved by subjecting the aqueous TG solution to sterile filtration.

[Addition of Bittern and TG]

The aqueous coagulant solution and the aqueous TG solution are added to the sterilized soybean milk. Natural bittern, magnesium chloride or magnesium sulfate is preferably added in an amount of 0.01 to 0.3 w/v %, and calcium chloride, calcium sulfate, calcium primary phosphate or calcium lactate is preferably added in an amount of 0.01 to 0.1 w/v %.

When two or more coagulants are used in combination, for example, where magnesium chloride and calcium chloride are combined, the amount of the magnesium salt to be added is not more than 0.3 w/v %, and that of the calcium salt is not more than 0.1 w/v %.

If the amount of the coagulant added exceeds the above range, the soybean protein coagulates immediately after the addition even if the soybean milk is cool, resulting in a brittle texture and an unpleasant taste with bitterness or astringency. If the amount of the coagulant is too small, coagulation would be difficult.

The amount of TG to be added is, in using for example TG having a specific activity of 2 U/mg, 0.05 to 2.5 mg, preferably 0.1 to 1.0 mg, per gram of the soybean milk protein. If too much TG is added, the resulting tofu becomes highly elastic, giving a texture like boiled egg white.

It is not until a specific amount of bittern (a coagulant) and a strictly limited amount of TG are combined that packed tofu excellent in flavor and texture can be obtained.

The order of adding the coagulant and TG is of importance. TG is added either simultaneously with or, for preference, after addition of the coagulant. If TG is added before the coagulant, the protein in soybean milk partially undergoes the enzymatic action of TG so that the subsequent addition of the coagulant tends to induce abrupt coagulation reaction under some conditions only to produce tofu with a rough texture.

The sterile soybean milk to which the coagulant, etc. are added is preferably kept at 2 to 15° C., particularly 5 to 10° C.

[Packing into Container]

After the addition of the coagulant and TG, the sterile soybean milk is packed into a container. Any container commonly used for packed tofi, such as a polypropylene container with a cover sheet of a nylon/unstretched polypropylene laminate, can be used.

The soybean milk in the sealed container is heated at a temperature of 70° C. or lower, preferably 35 to 70° C., for 5 to 120 minutes to cause enzymatic reaction and coagulation reaction simultaneously. Meanwhile the soybean milk becomes gel. Thereafter, the gel is further heated at 75° C. or higher, preferably 75 to 110° C. for 5 to 120 minutes to deactivate the enzyme and, at the same time, to complete the coagulation reaction, followed by cooling to obtain a final product. In the production of sterile packed tofu, the addition of a sterilized coagulant and TG, filling in a sterilized container, and sealing of the container are carried out in a sterile atmosphere.

The present invention will now be illustrated in greater detail with reference to Test Example and Examples. Unless otherwise noted, all the percents are by weight.

TEST EXAMPLE

Preparation of Sterile Soybean Milk 100 kg of whole soybeans were washed with water, soaked in water overnight, and ground in a horizontal grinder while pouring 400 l of water. Immediately after grinding, the slurry was heated in a heater provided in the discharge pipe of the grinder at 105° C. for 30 seconds. After cooling to 80° C., the solid matter was separated by means of a screw decanter. The resulting soybean milk was degassed in a vacuum container (degree of vacuum: 65 mmHg), followed by cooling to 10° C.

The cooled soybean milk was heated to 90° C. by indirect heating, and clean steam was blown therein to heat it to 140° C., at which the soybean milk was kept for 2 seconds. The soybean milk thus sterilized was introduced into a vacuum container, where it was cooled to around 90° C. to remove the water content of the blown steam to restore the initial soybean milk concentration, and then further cooled to 10° C. The resulting sterile soybean milk had a protein content of 6.5%.

Preparation of Coagulant Solution and TG Solution (a) A 45% aqueous solution of magnesium chloride ($MgCl_2.6H_2O$), (b) a 45% aqueous solution of calcium chloride ($CaCl_2.2H_2O$), and (c) a 20% aqueous solution of calcium lactate [$(CH_3CHOHCOO)_2Ca.5H_2O$] were prepared. A 50% aqueous solution of TG (KS-TK2, produced by Ajinomoto Co., Ltd.; 20 U/g) was prepared.

Preparation of Packed Tofu

To 300 ml of the sterile soybean milk (10° C.) were added the coagulant solution and the TG solution in this order in amounts shown in Table 1 below, and the mixture was packed into a 300 ml-volume plastic container and sealed. Immediately after sealing, the mixture was heated in warm water at 60° C. for 60 minutes to induce an enzymatic reaction and then heated in hot water at 80° C. for 30 minutes to deactivate TG and to complete coagulation simultaneously. The resulting tofu samples were designated sample Nos. 1 to 8. Tofu sample Nos. 9 and 10 were prepared in accordance with Examples of Japanese Patent Laid-Open No. 241168/95, in which sealed sterile soybean milk to which a coagulant and TG had been added was coagulated not by heating but by maintaining at 20° C. for 60 hours (sample No. 9) or 120 hours (sample No. 10).

The resulting packed tofu was cooled with cold water and put in a refrigerator at 5° C. overnight. The hardness and texturopattern of the samples after the storage were measured in accordance with the following method.

Five 17-mm cubes were cut out of each sample, and the cube was pressed with a disc plunger (diameter: 40 mm) in Tensipresser (manufactured by Taketomo Electric Inc.). The average of total stress until rupture (erg/cm$^2$) (n=5) was taken as the hardness of tofu. The texturopattern of sample Nos. 4 to 10, which is the plot of stress imposed until the disc plunger is pressed into a depth of 12 mm, are shown in FIGS. 1 through 7.

Further, the palatability of the samples was evaluated organoleptically in terms of stingingness and bitterness. The results of the measurement and evaluation are shown in Table 1.

The cooled soybean milk was heated to 90° C. indirectly, and clean steam was blown therein to heat it to 145° C., at which the soybean milk was kept for 2 seconds. The soybean milk thus sterilized was introduced into a vacuum container, where it was cooled to around 90° C. to remove the water content of the blown steam to restore the initial soybean milk concentration, and then further cooled to 10° C. The resulting sterile soybean milk had a protein content of 6.6%.

A 50% aqueous solution of natural bittern (magnesium content: 61,000 ppm; calcium content: 300 ppm) was preliminarily filtered through filter paper containing diatomite and then sterilely filtered through a filter having a pore size of 0.22 μm (a product of Nippon Millipore K.K.). The resulting solution was added to the sterile soybean milk in an amount of 6 ml per liter of the soybean milk and mixed. A 20% aqueous TG solution having been subjected to sterile filtration in the same manner as described above was then added in an amount of 10 ml per liter of the soybean milk and mixed. The resulting mixture was packed into a 300 ml-volume plastic container and, immediately after the sealing, the container was kept in warm water at 50° C. for 60 minutes to conduct an enzymatic reaction. Then the

TABLE 1

Figure 1:
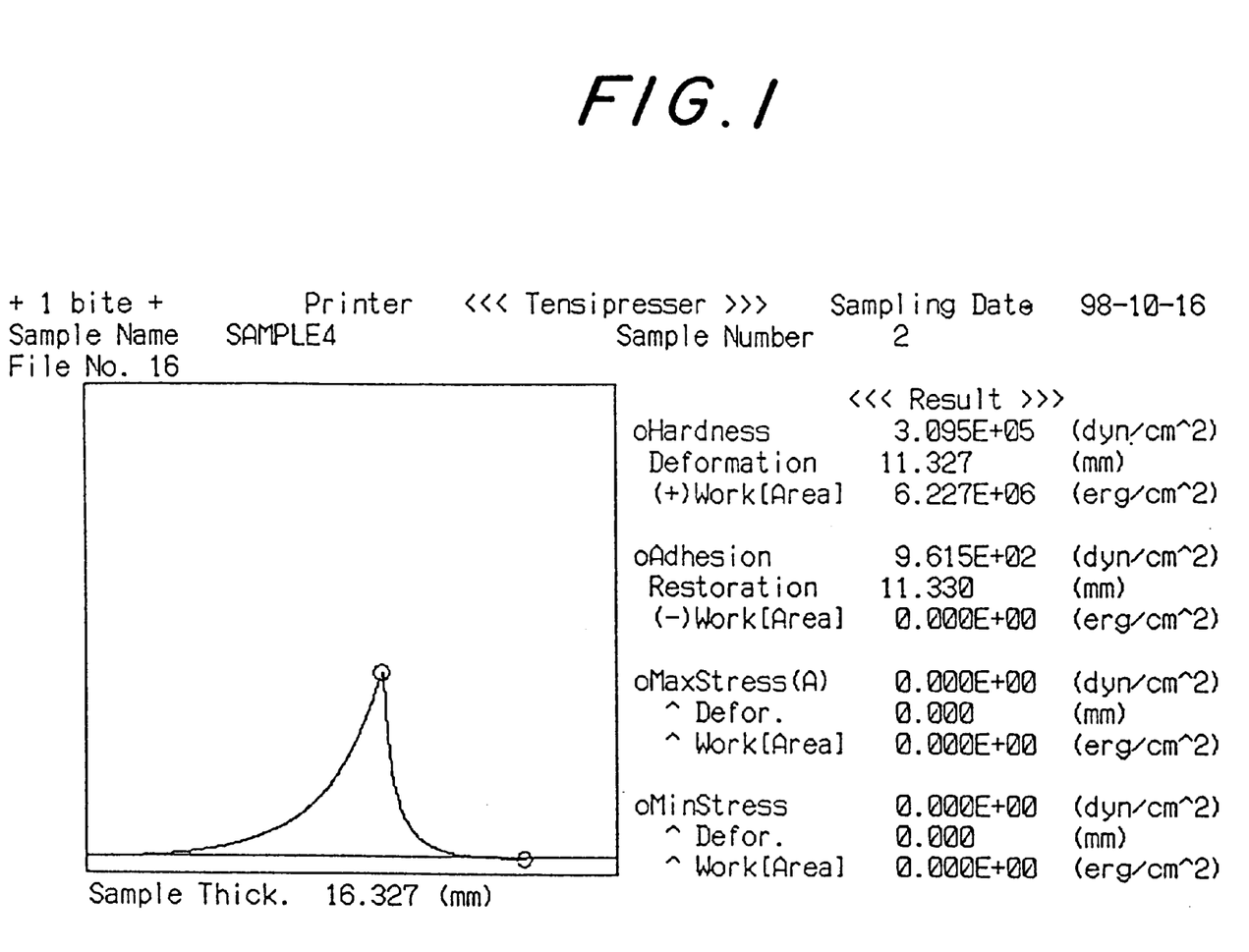
FIG. 1 shows a texturopattern of tofu sample No. 4 prepared in Test Examples.
Figure 2:
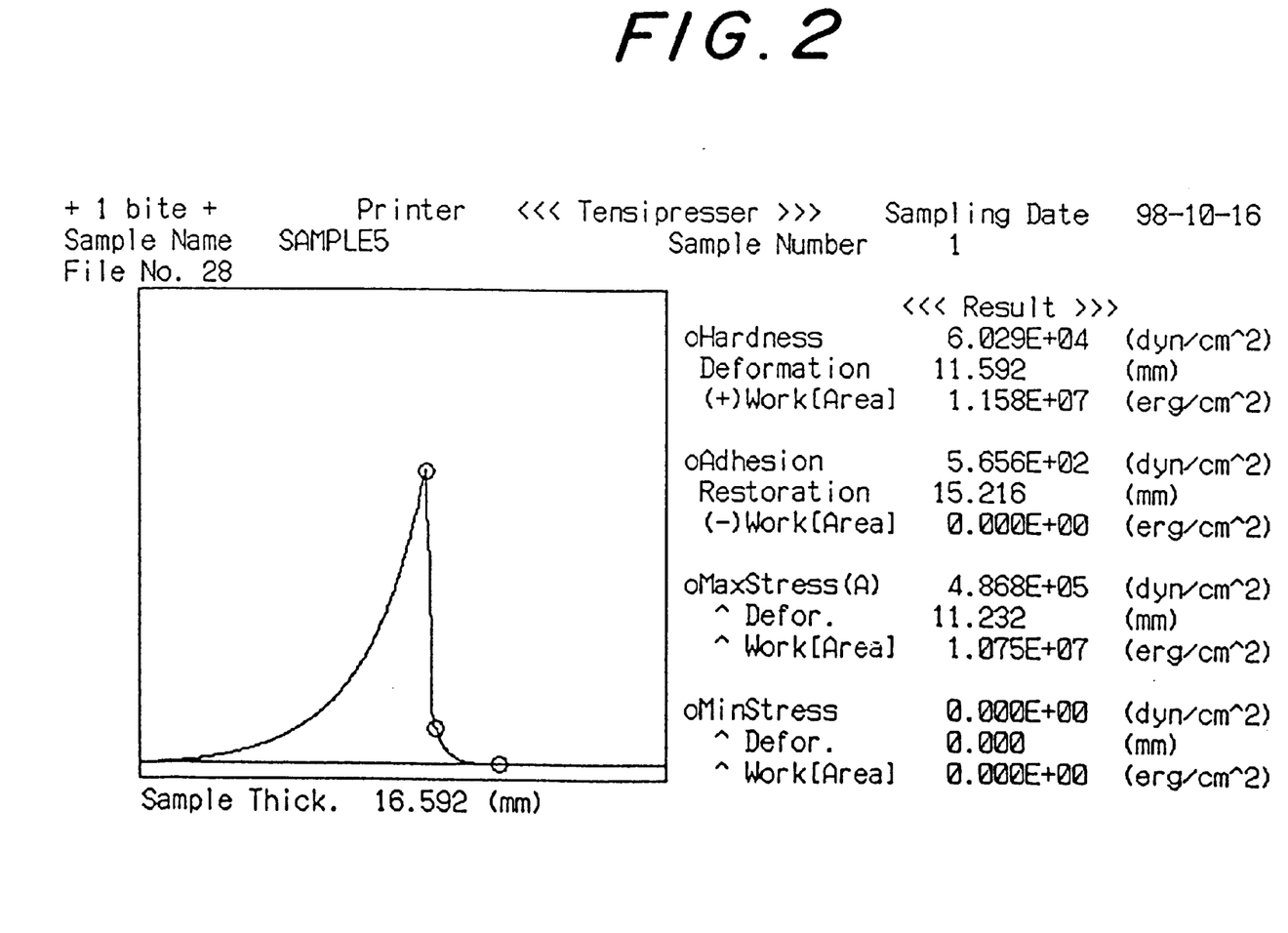
FIG. 2 shows a texturopattern of tofu sample No. 5 prepared in Test Examples.
Figure 3:
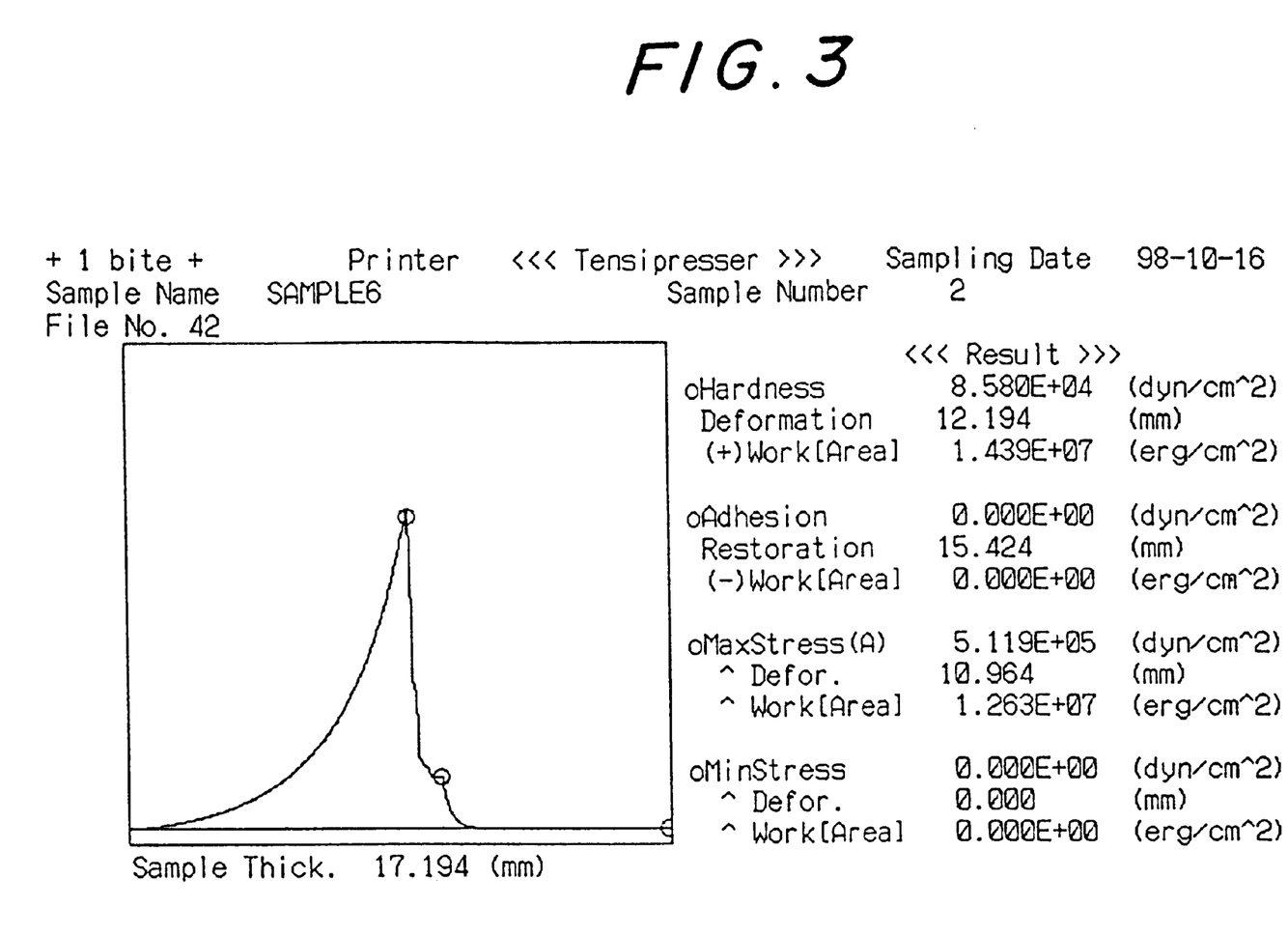
FIG. 3 shows a texturopattern of tofu sample No. 6 prepared in Test Examples.
Figure 4:
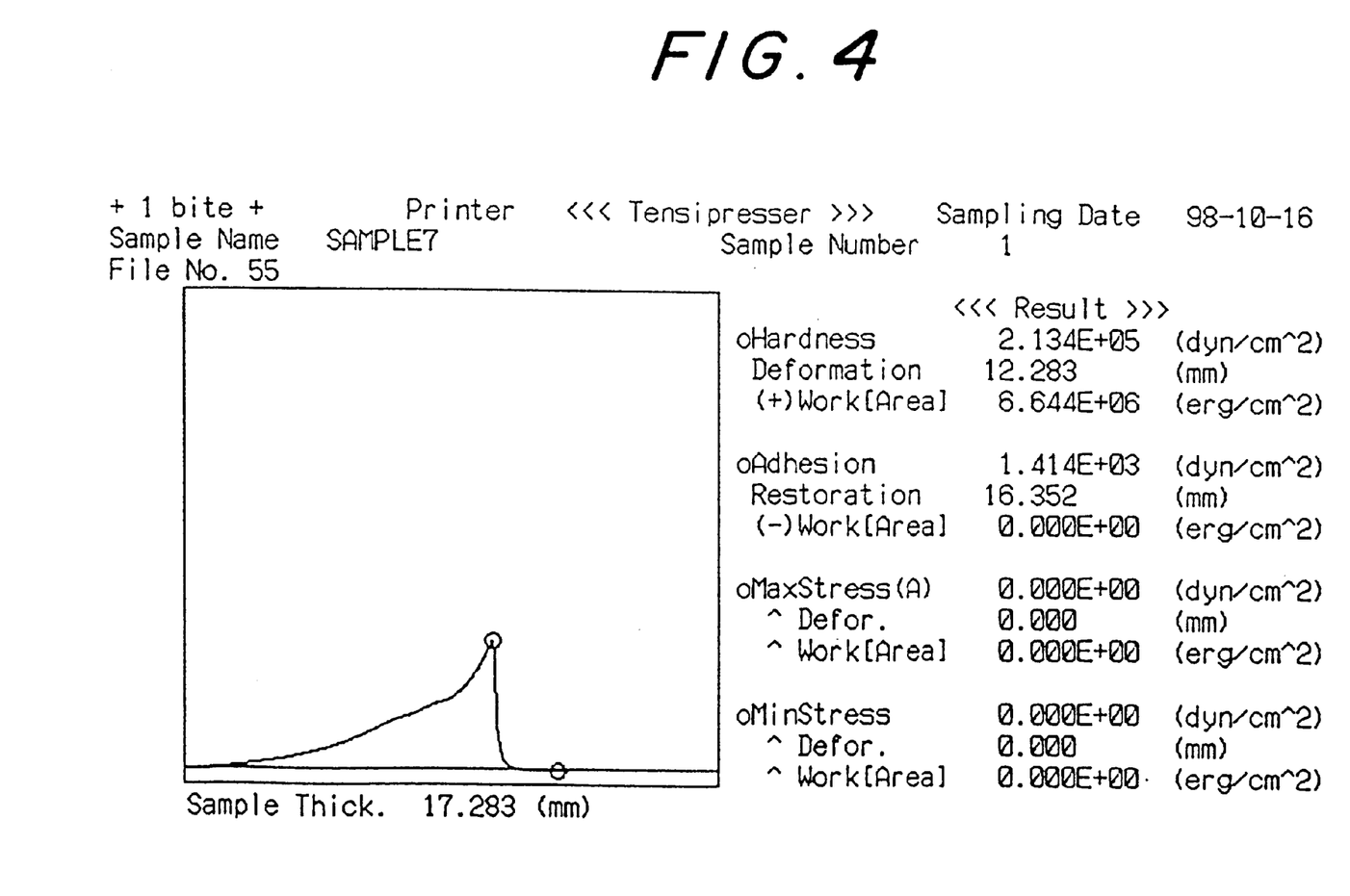
FIG. 4 shows a texturopattern of tofu sample No. 7 prepared in Test Examples.
Figure 5:
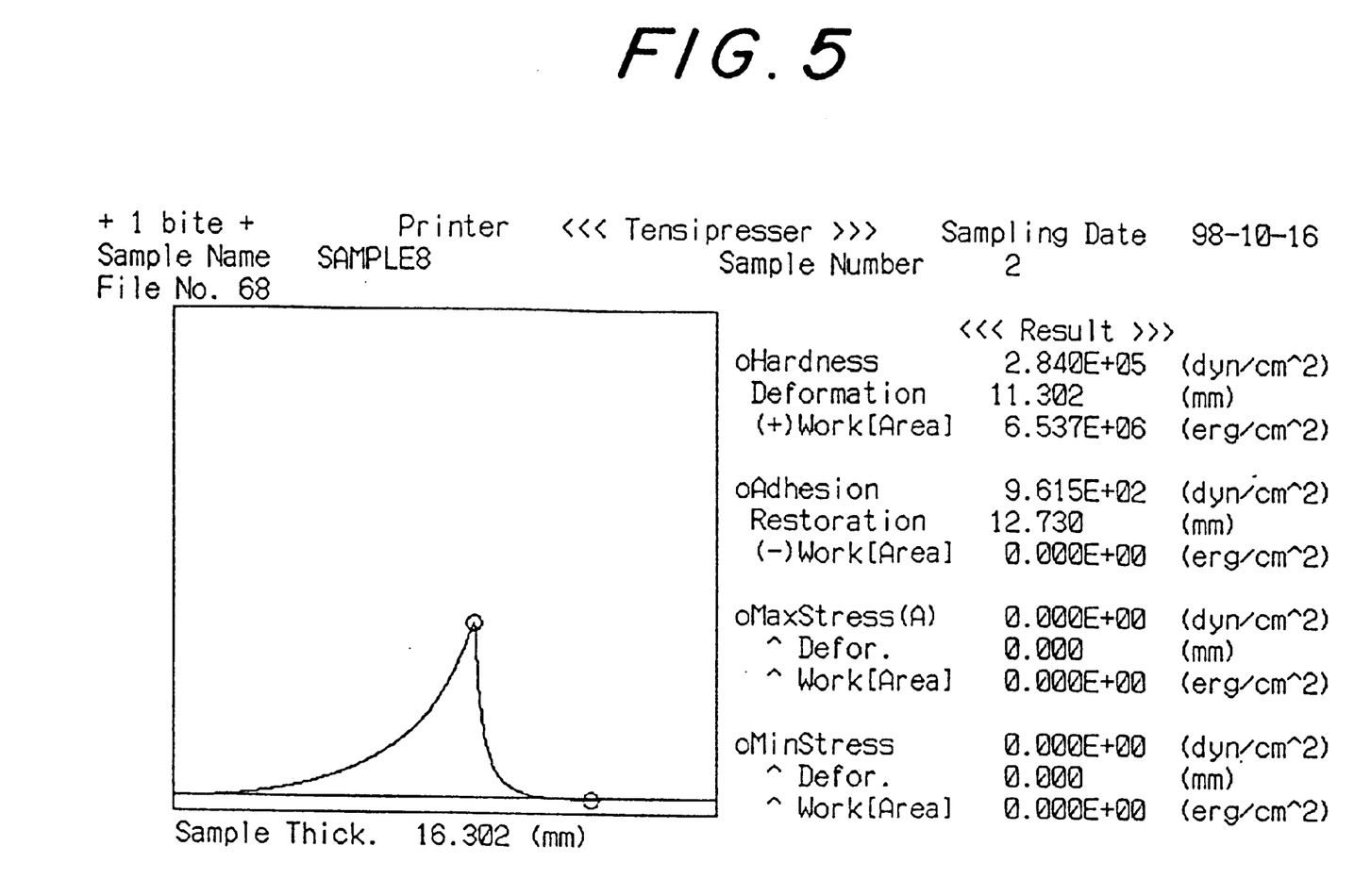
FIG. 5 shows a texturopattern of tofu sample No. 8 prepared in Test Examples.
Figure 6:
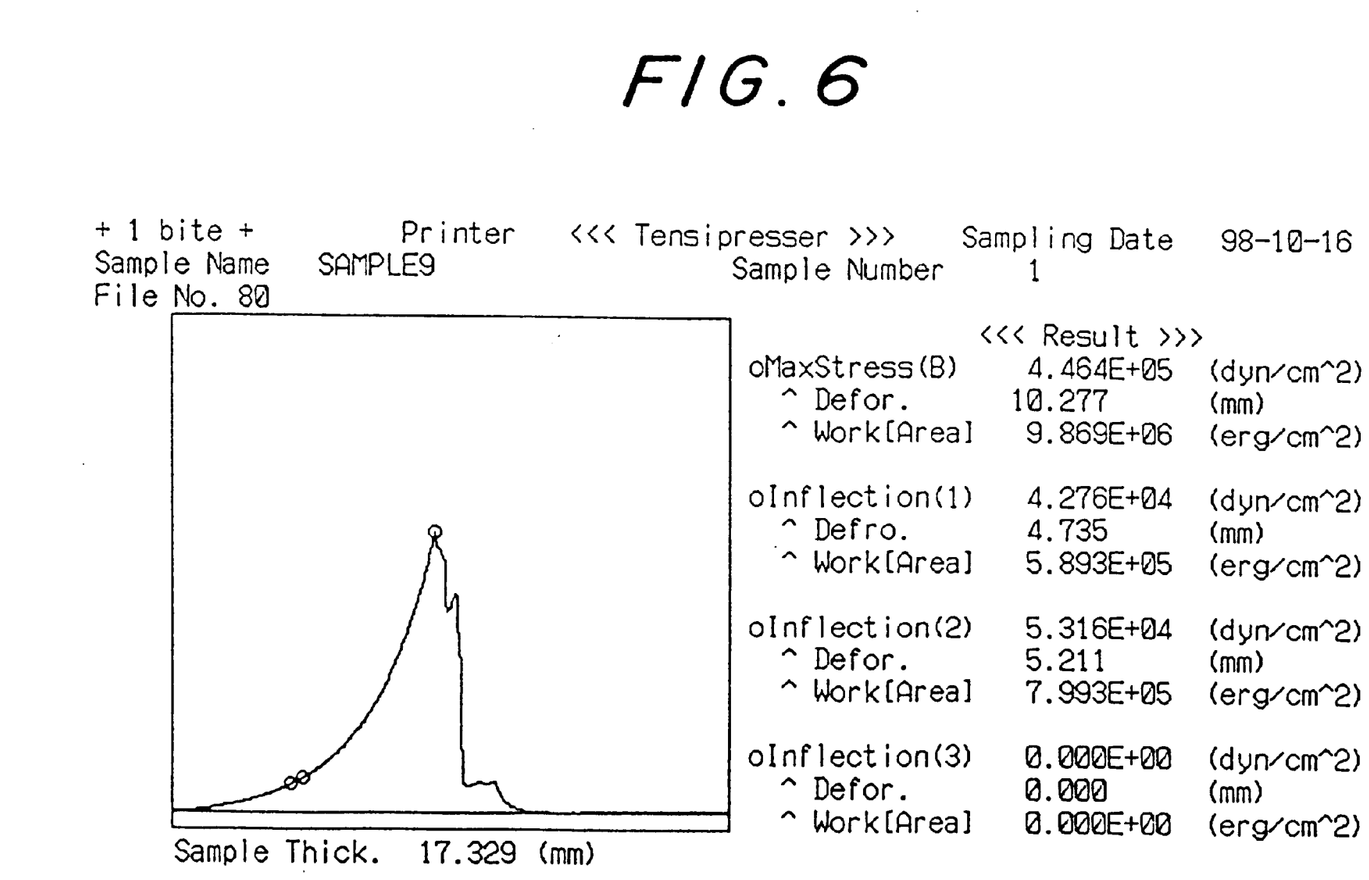
FIG. 6 shows a texturopattern of tofu sample No. 9 prepared in Test Examples.
Figure 7:
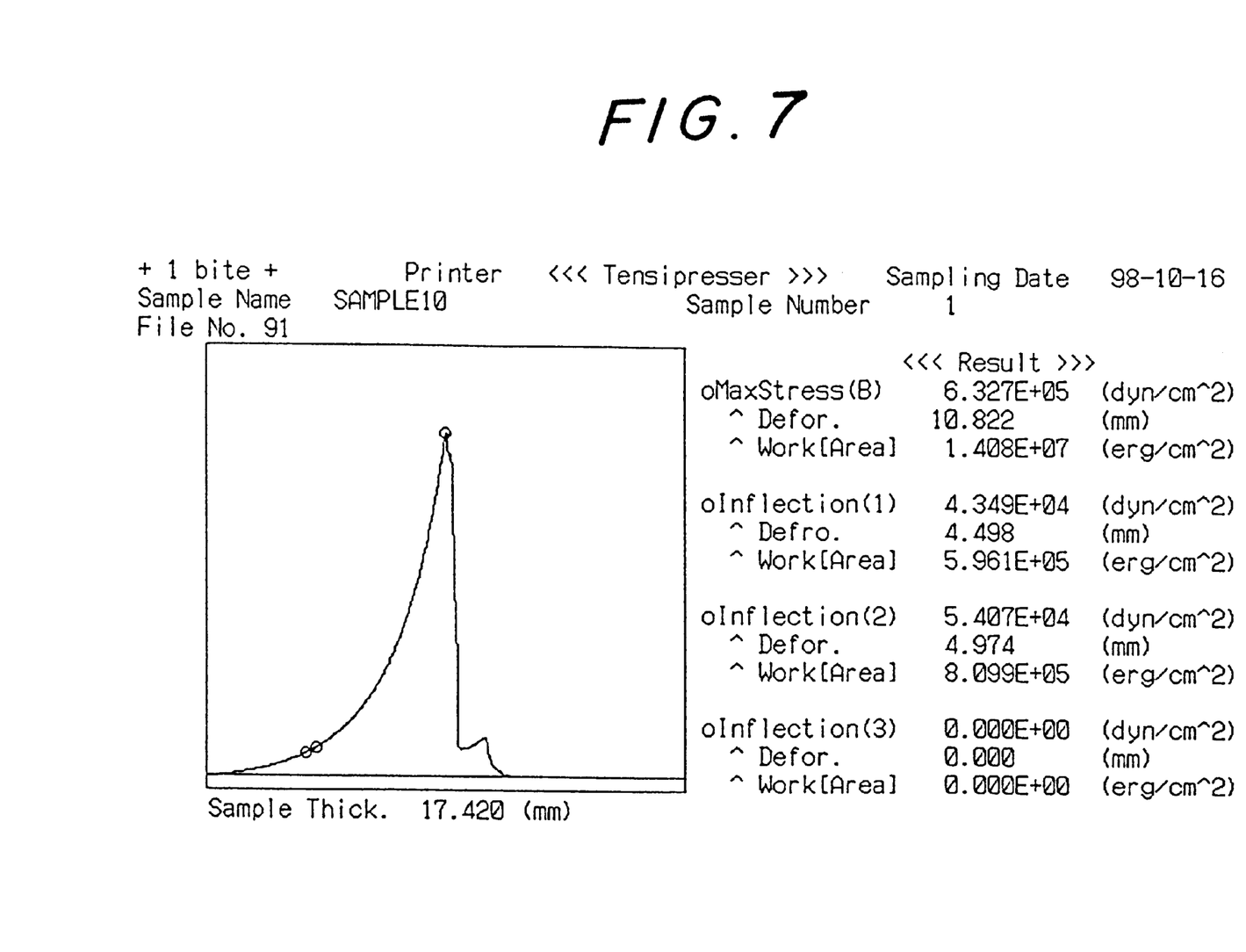
FIG. 7 shows a texturopattern of tofu sample No. 10 prepared in Test Examples.

| Sample No. | (a) (ml) | (b) (ml) | (c) (ml) | TG (ml) | Hardness (× 10$^6$ erg/cm$^2$) | Palatability* String-ingness | Bitter-ness | Texturo-pattern |
| --- | --- | --- | --- | --- | --- | --- | --- | --- |
| 1 | 1.3 | 0.4 | – | – | 1.57 | – | – | |
| 2 | 2.5 | 1.0 | – | – | unmeasurable | + | + | |
| 3 | – | – | – | 1.2 | unmeasurable | – | – | |
| 4 | – | – | – | 12.0 | 6.09 | – | – | FIG. 1 |
| 5 | 1.3 | 0.4 | – | 12.0 | 12.20 | – | – | FIG. 2 |
| 6 | 2.5 | 1.0 | – | 12.0 | 11.20 | + | + | FIG. 3 |
| 7 | 2.5 | 1.0 | – | 1.2 | 5.10 | + | + | FIG. 4 |
| 8 | 1.3 | 0.4 | – | 1.2 | 6.45 | – | – | FIG. 5 |
| 9 | 2.0 | – | 1.5 | 19.5 | 12.10 | + | + | FIG. 6 |
| 10 | 2.0 | – | 1.5 | 19.5 | 14.40 | + | + | FIG. 7 |

Note: *Palatability was judged - (stingingness or bitterness was not felt) or + (felt). Bitterness was felt strong at a high magnesium chloride content, and stingingness was felt strong at a high calcium chloride content.

As is apparent from Table 1, the packed tofu prepared by the process of the present invention (sample No. 8) is excellent in both hardness and flavor. It gave off no bad odor even when stored in a home refrigerator for 30 days, whereas commercially available packed tofu emitted an unpleasant odor on the 5th day of the storage.

For reference, hardness of 20 kinds each of packed tofu and cut tofu purchased at the market was measured in the same manner as described above. As a result, the average hardness of the packed tofu and the cut tofu was found to be 4.3×10$^6$ erg/cm$^2$ and 2.8×10$^6$ erg/cm$^2$, respectively, from which the hardness for keeping the texture as tofu seems to be from 2.5 to 5.0×10$^6$ erg/cm$^2$.

EXAMPLE 1

300 kg of whole soybeans were washed with water, soaked in water overnight, and ground at low temperature in a horizontal grinder while pouring 1100 l of water at 5° C. Immediately after grinding, the resulting slurry was heated in a heater provided in the discharge pipe of the grinder at 108° C. for 30 seconds. After cooling to 90° C., the solid matter was separated by means of a screw decanter. The resulting soybean milk was degassed in a vacuum container (degree of vacuum: 65 mmHg), followed by cooling to 10° C.

container was put in hot water at 95° C. for 30 minutes to deactivate the enzyme and, at the same time, to complete coagulation, followed by cooling with cold water to obtain a packed tofu product.

The resulting tofu had a hardness of 3.22×10$^6$ erg/cm$^2$ as measured in the same manner as in Test Example and had a satisfactory palatability without stingingness nor bitterness. Even when stored in a home refrigerator for 60 days, no change in palatability was observed.

EXAMPLE 2

Sterile packed tofu was prepared in the same manner as in Example 1, except that the addition and mixing of the natural bittern solution and the TG solution and the packing into the container were carried out in a sterile atmosphere and that the container had been sterilized. The resulting sterile tofu underwent no change in palatability even when stored at room temperature for 30 days.

What is claimed is:

1. A process for producing packed tofu which comprises the steps of mixing soybean milk having been heat-sterilized at 130° C. to 160° C. and cooled with (A) 0.01 to 0.3% by weight by volume of at least one coagulant selected from the group consisting of natural bittern, magnesium chloride, magnesium sulfate, calcium chloride, calcium primary phosphate, calcium sulfate, and calcium lactate and (B) 0.1 to 5 units, per gram of soybean milk protein, of transglutaminase either simultaneously or in the order (A) then (B) as stated, then packing and sealing the mixture in a container, thereafter coagulating the mixture in the sealed container at a temperature of 70° C. or lower by the action of the coagulant and transglutaminase, and thereafter heating the coagulated mixture to 75° C. or higher in the sealed container to deactivate the transglutaminase and to complete the coagulation by the coagulant.

2. The process according to claim 1, wherein said coagulation by the action of the coagulant and transglutaminase is carried out at 35 to 70° C. for 5 to 120 minutes in the sealed container, and said heating to deactivate the transglutaminase and to complete the coagulation is carried out at 75 to 110° C. for 5 to 120 minutes in the sealed container.

3. The process according to claim 1, wherein said coagulant is a sterilized coagulant, and said mixing is carried out in a sterile atmosphere.

4. A process for producing sterile packed tofu which comprises the steps of mixing soybean milk having been heat-sterilized at 130° C. and 160° C. and cooled with (A) 0.01 to 0.3% by weight by volume of at least one sterilized coagulant selected from the group consisting of natural bittern, magnesium chloride, magnesium sulfate, calcium chloride, and calcium primary phosphate and (B) 0.1 to 5 units, per gram of soybean milk protein, of transglutaminase either simultaneously or in the order (A) then (B) as stated, in a sterile atmosphere, then packing and sealing the mixture in a container in a sterile atmosphere, thereafter maintaining the mixture at 35 to 70° C. for 5 to 120 minutes in the sealed container to allow the mixture to coagulate by the action of the coagulant and transglutaminase, and thereafter heating the coagulated mixture at 75 to 110° C. for 5 to 120 minutes in the sealed container to deactivate the transglutaminase and to complete the coagulation by the coagulant.

* * * * *